United States Patent
Hartley

(10) Patent No.: US 10,166,095 B2
(45) Date of Patent: *Jan. 1, 2019

(54) INTRODUCER FOR A SIDE BRANCH DEVICE

(71) Applicant: Cook Medical Technologies LLC, Bloomington, IN (US)

(72) Inventor: David Ernest Hartley, Wannanup (AU)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,235

(22) Filed: Sep. 20, 2017

(65) Prior Publication Data

US 2018/0008395 A1 Jan. 11, 2018

Related U.S. Application Data

(60) Division of application No. 13/181,285, filed on Jul. 12, 2011, now Pat. No. 9,770,321, which is a division
(Continued)

(51) Int. Cl.
*A61F 2/07* (2013.01)
*A61F 2/954* (2013.01)
(Continued)

(52) U.S. Cl.
CPC ............... *A61F 2/07* (2013.01); *A61F 2/954* (2013.01); *A61F 2/89* (2013.01); *A61F 2/962* (2013.01);
(Continued)

(58) Field of Classification Search
CPC .... A61F 2/07; A61F 2/954; A61F 2/89; A61F 2/962; A61F 2002/061; A61F 2002/067; A61F 2002/075; A61F 2002/9511
See application file for complete search history.

(56) References Cited

U.S. PATENT DOCUMENTS 5,387,235 A * 2/1995 Chuter ............... A61B 17/0469
606/194
5,628,783 A 5/1997 Quiachon et al.
(Continued)

FOREIGN PATENT DOCUMENTS

EP 0508473 A2 10/1992
EP 0684022 A2 11/1995
(Continued)

OTHER PUBLICATIONS

International Search Report and Written Opinion for PCT/US2004/033566 dated May 24, 2005, 8 pages.
(Continued)

*Primary Examiner* — Jing Ou
(74) *Attorney, Agent, or Firm* — Brinks Gilson & Lione

(57) ABSTRACT

An introduction arrangement for a fenestrated or branched stent graft (13) intended for deployment into the lumen of a vessel having a blind vessel extending from it. The introducer (1) has a distal end intended to remain outside a patient in use and a proximal end with a nose cone dilator (11) and an arrangement to retain the branched stent graft distally of the nose cone dilator. A sheath (15) on the introducer extends over the branched stent graft to the nose cone dilator. An indwelling catheter (21) extends from the distal end of the introducer and enters the fenestration or side arm and through to the nose cone dilator, the indwelling catheter has a guide wire (29) extending through it. The guide wire can be extended beyond the nose cone dilator in use before the sheath is withdrawn from the branched stent graft so that it can be snared from the contra-lateral artery.

20 Claims, 12 Drawing Sheets

Related U.S. Application Data of application No. 11/713,388, filed on Mar. 2, 2007, now Pat. No. 7,998,186, which is a continuation-in-part of application No. 10/962,763, filed on Oct. 12, 2004, now Pat. No. 8,012,193.

(60) Provisional application No. 60/778,571, filed on Mar. 2, 2006, provisional application No. 60/601,485, filed on Aug. 13, 2004, provisional application No. 60/510,823, filed on Oct. 14, 2003.

(51) Int. Cl.
  *A61F 2/962* (2013.01)
  *A61F 2/06* (2013.01)
  *A61F 2/95* (2013.01)
  *A61F 2/89* (2013.01)

(52) U.S. Cl.
  CPC ... *A61F 2002/061* (2013.01); *A61F 2002/067* (2013.01); *A61F 2002/075* (2013.01); *A61F 2002/9511* (2013.01)

(56) References Cited

U.S. PATENT DOCUMENTS

| | | |
|---|---|---|
| 5,669,924 A | 9/1997 | Shaknovich |
| 5,676,696 A | 10/1997 | Marcade |
| 5,683,450 A | 11/1997 | Goicoechea |
| 5,693,085 A | 12/1997 | Baker et al. |
| 5,720,776 A | 2/1998 | Chuter et al. |
| 5,776,142 A | 7/1998 | Gunderson |
| 5,824,055 A | 10/1998 | Spiridigliozzi et al. |
| 5,984,955 A | 11/1999 | Wisselink |
| 6,162,246 A | 12/2000 | Barone |
| 6,187,033 B1 | 2/2001 | Schmitt |
| 6,206,931 B1 | 3/2001 | Cook et al. |
| 6,325,826 B1 | 12/2001 | Vardi et al. |
| 6,428,565 B1 | 8/2002 | Wisselink |
| 6,524,335 B1 | 2/2003 | Hartley et al. |
| 6,645,242 B1 * | 11/2003 | Quinn ................. A61F 2/07 623/1.13 |
| 6,660,030 B2 | 12/2003 | Shaolian et al. |
| 6,663,666 B1 | 12/2003 | Quiachon et al. |
| 6,695,875 B2 | 2/2004 | Stelter et al. |
| 6,827,726 B2 | 12/2004 | Parodi |
| 6,858,038 B2 | 2/2005 | Heuser |
| 6,939,370 B2 | 9/2005 | Hartley et al. |
| 6,949,121 B1 * | 9/2005 | Laguna ................. A61F 2/07 623/1.35 |
| 6,974,471 B2 | 12/2005 | Van Schie et al. |
| 7,014,653 B2 | 3/2006 | Ouriel et al. |
| 7,232,459 B2 | 6/2007 | Greenberg et al. |
| 7,238,198 B2 | 7/2007 | Hartley et al. |
| 7,294,147 B2 | 11/2007 | Hartley |
| 7,722,657 B2 | 5/2010 | Hartley |
| 7,803,177 B2 | 9/2010 | Hartley et al. |
| 7,998,186 B2 * | 8/2011 | Hartley ................. A61F 2/07 623/1.11 |
| 8,012,193 B2 * | 9/2011 | Hartley ................. A61F 2/07 623/1.11 |
| 9,770,321 B2 * | 9/2017 | Hartley ................. A61F 2/07 |
| 2001/0007954 A1 | 7/2001 | Shaolian et al. |
| 2001/0012943 A1 | 8/2001 | Shaolian et al. |
| 2001/0014823 A1 | 8/2001 | Ressemann et al. |
| 2001/0016767 A1 | 8/2001 | Wilson et al. |
| 2001/0020184 A1 | 9/2001 | Dehdashtian et al. |
| 2001/0037141 A1 | 11/2001 | Yee et al. |
| 2001/0037142 A1 * | 11/2001 | Stelter ................. A61F 2/07 623/1.13 |
| 2001/0049548 A1 * | 12/2001 | Vardi ................. A61F 2/954 623/1.11 |
| 2002/0019665 A1 | 2/2002 | Dehdashtian et al. |
| 2002/0045930 A1 | 4/2002 | Burg et al. |
| 2002/0077591 A1 * | 6/2002 | Happ ................. A61F 2/958 604/96.01 |
| 2002/0099436 A1 | 7/2002 | Thornton |
| 2002/0143383 A1 | 10/2002 | Parodi |
| 2002/0151953 A1 | 10/2002 | Chobotov et al. |
| 2002/0156518 A1 * | 10/2002 | Tehrani ................. A61F 2/07 623/1.11 |
| 2002/0173835 A1 | 11/2002 | Bourang |
| 2003/0088305 A1 | 5/2003 | Van Schie et al. |
| 2003/0120332 A1 | 6/2003 | Hartley |
| 2003/0120333 A1 | 6/2003 | Ouriel et al. |
| 2003/0135257 A1 | 7/2003 | Taheri |
| 2003/0153969 A1 | 8/2003 | Dehdashtian et al. |
| 2003/0167083 A1 | 9/2003 | Lashinski et al. |
| 2003/0181923 A1 | 9/2003 | Vardi |
| 2003/0199967 A1 * | 10/2003 | Hartley ................. A61F 2/07 623/1.13 |
| 2003/0233140 A1 | 12/2003 | Hartley et al. |
| 2004/0054396 A1 | 3/2004 | Hartley et al. |
| 2004/0073289 A1 | 4/2004 | Hartley |
| 2004/0082990 A1 | 4/2004 | Hartley |
| 2004/0098079 A1 | 5/2004 | Hartley et al. |
| 2004/0106978 A1 | 6/2004 | Greenberg et al. |
| 2004/0143286 A1 | 7/2004 | Johnson |
| 2004/0230287 A1 * | 11/2004 | Hartley ................. A61F 2/07 623/1.12 |
| 2006/0178733 A1 | 8/2006 | Pinchuk |

FOREIGN PATENT DOCUMENTS

| | | |
|---|---|---|
| EP | 0904745 A2 | 3/1999 |
| WO | WO98/53761 | 12/1998 |
| WO | WO99/29262 | 6/1999 |
| WO | WO99/44539 | 9/1999 |
| WO | WO01/67993 A2 | 9/2001 |
| WO | WO03/34948 | 5/2003 |
| WO | WO03/53287 | 7/2003 |
| WO | WO03/101518 | 12/2003 |
| WO | WO04/02365 | 1/2004 |
| WO | WO04/02370 | 1/2004 |
| WO | WO04/17867 | 3/2004 |
| WO | WO04/17868 | 3/2004 |
| WO | WO04/28399 | 4/2004 |

OTHER PUBLICATIONS

Restriction Requirement dated Apr. 1, 2008 for U.S. Appl. No. 10/962,763, 6 pages.
Response to Restriction Requirement dated May 23, 2008 for U.S. Appl. No. 10/962,763, 8 pages.
Office Action dated Jul. 8, 2008 for U.S. Appl. No. 10/962,763, 11 pages.
Response to Office Action dated Oct. 14, 2008 for U.S. Appl. No. 10/962,763, 10 pages.
Final Office Action dated Jan. 12, 2009 for U.S. Appl. No. 10/962,763, 7 pages.
Response to Final Office Action dated Feb. 25, 2009 for U.S. Appl. No. 10/962,763, 9 pages.
Advisory Action dated Apr. 1, 2009 for U.S. Appl. No. 10/962,763, 3 pages.
Request for Continued Examination dated Apr. 13, 2009 for U.S. Appl. No. 10/962,763, 9 pages.
Office Action dated May 8, 2009 for U.S. Appl. No. 10/962,763, 6 pages.
Response to Office Action dated Aug. 10, 2009 for U.S. Appl. No. 10/962,763, 9 pages.
Final Office Action dated Nov. 18, 2009 for U.S. Appl. No. 10/962,763, 8 pages.
Response to Final Office Action dated Jan. 11, 2010 for U.S. Appl. No. 10/962,763, 9 pages.
Advisory Action dated Jan. 26, 2010 for U.S. Appl. No. 10/962,763, 3 pages.
Response to Advisory Action dated Feb. 8, 2010 for U.S. Appl. No. 10/962,763, 6 pages.

(56) References Cited

OTHER PUBLICATIONS

Advisory Action dated Mar. 2, 2010 for U.S. Appl. No. 10/962,763, 3 pages.
Request for Continued Examination dated Mar. 24, 2010 for U.S. Appl. No. 10/962,763, 8 pages.
Office Action dated May 10, 2010 for U.S. Appl. No. 10/962,763, 9 pages.
Response to Office Action dated Jul. 16, 2010 for U.S. Appl. No. 10/962,763, 9 pages.
Final Office Action dated Oct. 25, 2010 for U.S. Appl. No. 10/962,763, 8 pages.
Examiner Interview Summary dated Nov. 22, 2010 for U.S. Appl. No. 10/962,763, 4 pages.
Pre-Brief Conference Request dated Jan. 25, 2011 for U.S. Appl. No. 10/962,763, 7 pages.
Response to Final Office Action dated Jan. 25, 2011 for U.S. Appl. No. 10/962,763, 9 pages.
Advisory Action dated Feb. 3, 2011 for U.S. Appl. No. 10/962,763, 2 pages.
Response to Advisory Action dated Feb. 14, 2011 for U.S. Appl. No. 10/962,763, 7 pages.
Advisory Action dated Mar. 2, 2011 for U.S. Appl. No. 10/962,763, 3 pages.
Pre-Brief Conference Decision dated Apr. 4, 2011 for U.S. Appl. No. 10/962,763, 2 pages.
Examiner Interview Summary dated Apr. 13, 2011 for U.S. Appl. No. 10/962,763, 5 pages.
Notice of Allowance dated Apr. 13, 2011 for U.S. Appl. No. 10/962,763, 4 pages.
Restriction Requirement dated Feb. 16, 2010 for U.S. Appl. No. 11/713,388, 6 pages.
Response to Restriction Requirement dated Mar. 11, 2010 for U.S. Appl. No. 11/713,388, 5 pages.
Office Action dated May 12, 2010 for U.S. Appl. No. 11/713,388, 12 pages.
Response to Office Action dated Jul. 16, 2010 for U.S. Appl. No. 11/713,388, 8 pages.
Final Office Action dated Oct. 26, 2010 for U.S. Appl. No. 11/713,388, 8 pages.
Response to Final Office Action dated Dec. 9, 2010 for U.S. Appl. No. 11/713,388, 6 pages.
Advisory Action dated Jan. 21, 2011 for U.S. Appl. No. 11/713,388, 3 pages.
Pre-Brief Conference Request dated Jan. 26, 2011 for U.S. Appl. No. 11/713,388, 8 pages.
Pre-Brief Conference Decision dated Apr. 5, 2011 for U.S. Appl. No. 11/713,388, 2 pages.
Notice of Allowance dated Apr. 14, 2011 for U.S. Appl. No. 11/713,388, 7 pages.
Office Action for corresponding EP 04794818.7 dated Dec. 10, 2012, 3 pages.
Examination Report for corresponding EP 04794818.7 dated Jul. 1, 2013, 4 pages.
Office Action for corresponding EP 04794818.7 dated Feb. 11, 2015, 3 pages.
Restriction Requirement for U.S. Appl. No. 14/469,247 dated May 28, 2015, 6 pages.
Restriction Requirement for U.S. Appl. No. 14/469,234 dated May 29, 2015, 6 pages.
Restriction Requirement for U.S. Appl. No. 13/181,249 dated Nov. 18, 2013, 7 pages.
Response to Restriction Requirement filed in U.S. Appl. No. 13/181,249 dated Dec. 18, 2013, 6 pages.
Office Action for U.S. Appl. No. 13/181,249 dated Apr. 8, 2014, 16 pages.
Response to Office Action filed in U.S. Appl. No. 13/181,249 dated Sep. 8, 2014, 15 pages.
Office Action for U.S. Appl. No. 13/181,249 dated Jan. 9, 2015, 9 pages.
Response to Office Action filed in U.S. Appl. No. 13/181,249 dated Apr. 9, 2015, 10 pages.
Amendment Accompanying an RCE filed in U.S. Appl. No. 13/181,249 dated Apr. 30, 2015, 9 pages.
Office Action for U.S. Appl. No. 13/181,249 dated Jul. 28, 2015, 10 pages.
Response to Office Action filed in U.S. Appl. No. 13/181,249 dated Jan. 26, 2016, 9 pages.
Response to Restriction Requirement filed in U.S. Appl. No. 14/469,247 dated Aug. 28, 2015, 9 pages.
Office Action for U.S. Appl. No. 14/469,247 dated Nov. 19, 2015, 16 pages.
Response to Restriction Requirement filed in U.S. Appl. No. 14/469,234 dated Aug. 31, 2015, 7 pages.
Office Action for U.S. Appl. No. 14/469,234 dated Oct. 21, 2015, 22 pages.
European Search Report for EP 16150466, dated Apr. 27, 2016, 6 pgs.
European Search Report for EP 16150469, dated Apr. 27, 2016, 7 pgs.
European Search Report for EP 16150468, dated Apr. 28, 2016, 8 pgs.
European Search Report for EP 16150470, dated Apr. 28, 2016, 7 pgs.
Final Office Action for U.S. Appl. No. 13/181,249 dated May 17, 2016, 16 pages.
Response to Final Office Action for U.S. Appl. No. 13/181,249 dated Aug. 17, 2016, 13 pages.
Final Office Action for U.S. Appl. No. 14/469,234 dated Jun. 28, 2016, 25 pages.
Response to Final Office Action for U.S. Appl. No. 14/469,234 dated Oct. 28, 2016, 8 pages.
Final Office Action for U.S. Appl. No. 14/469,247 dated Jul. 27, 2016, 11 pages.
Response to Final Office Action for U.S. Appl. No. 14/469,247 dated Oct. 27, 2016, 2 pages.
Notice of Allowance U.S. Appl. No. 14/469,247 dated Nov. 14, 2016, 12 pages.
Anderson, John Lennon, et al., "Endoluminal Aortic Grafting With Renal and Superior Mesenteric Artery Incorporation by Graft Fenestration," *International Society of Endovascular Specialists*, 2001, 8, pp. 3-15.
Stanley, Brendan, et al., "Fenestration in Endovascular Grafts for Aortic Aneurysm Repair: New Horizons for Preserving Blood Flow in Branch Vessels," *International Society of Endovascular Specialists*, 2001, 8, pp. 16-24.

* cited by examiner

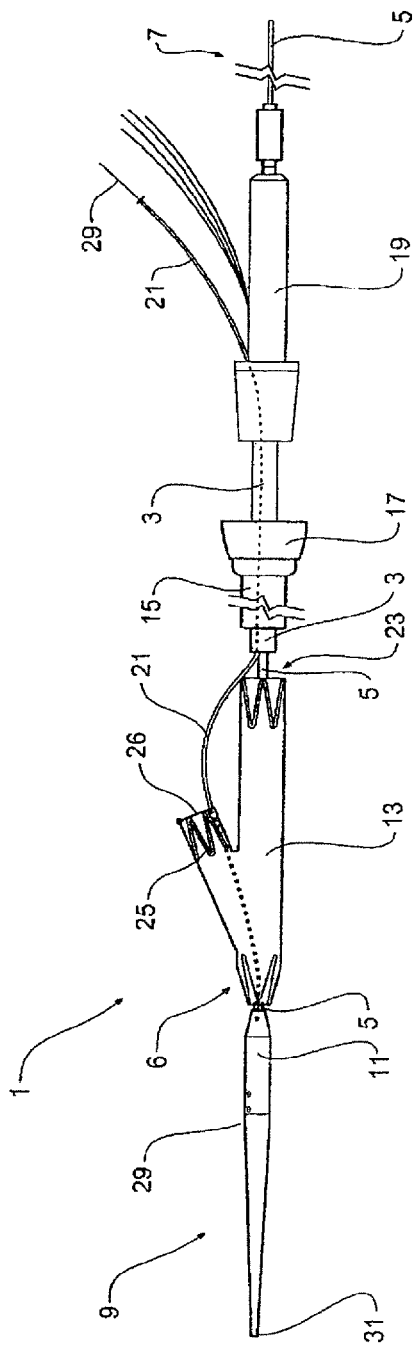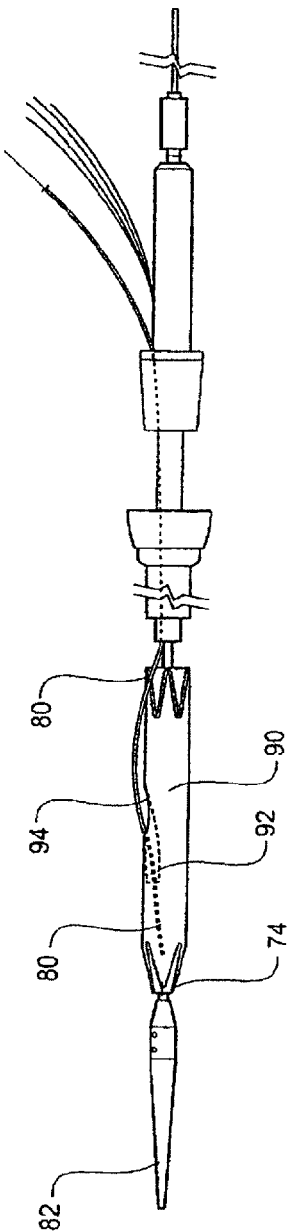
Fig 7
Fig 11

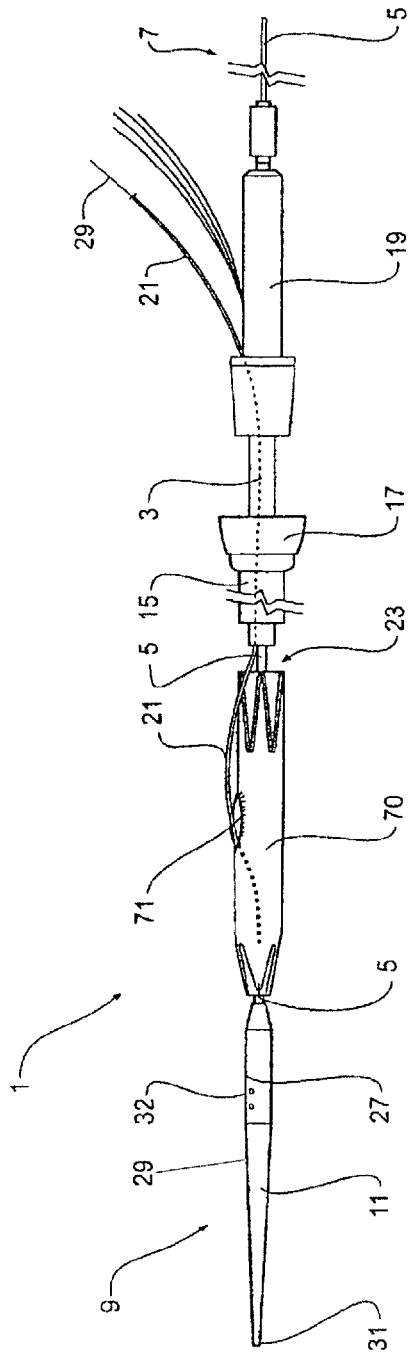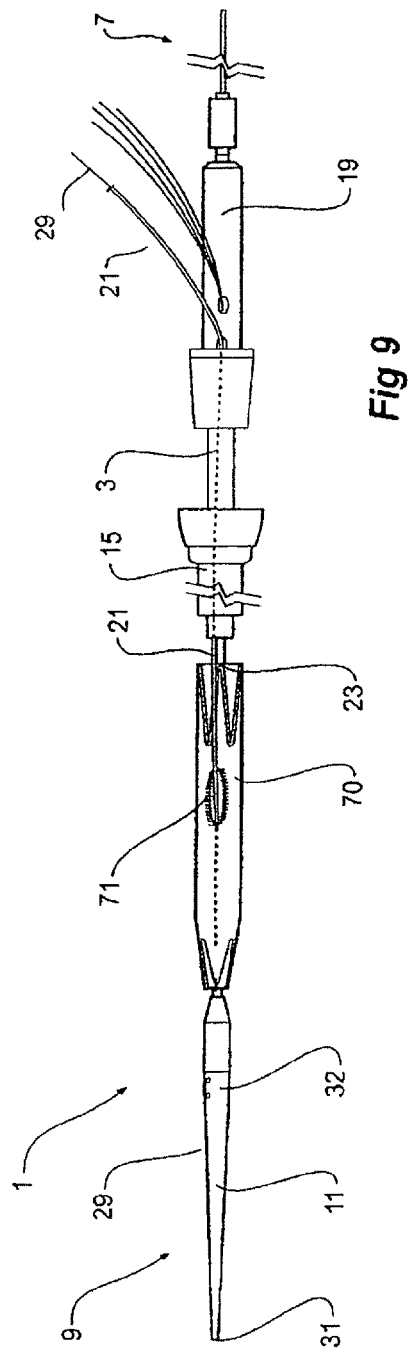

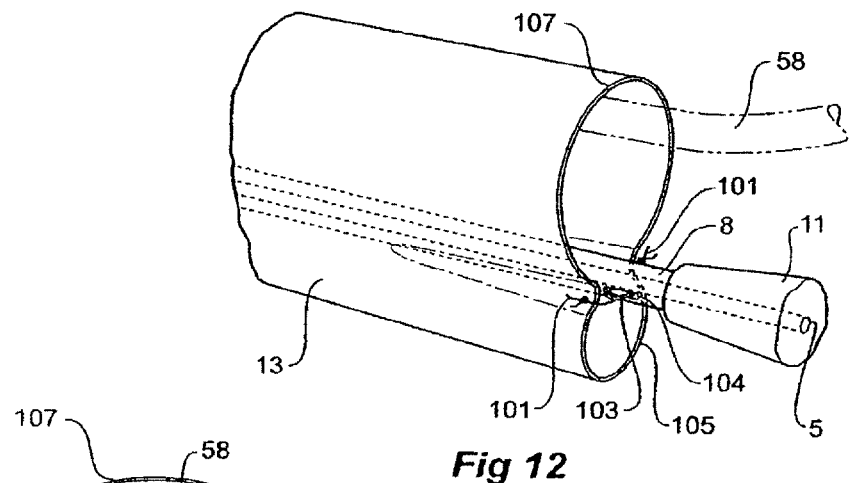
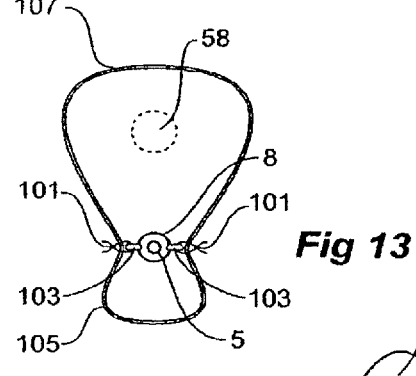
Fig 12
Fig 13
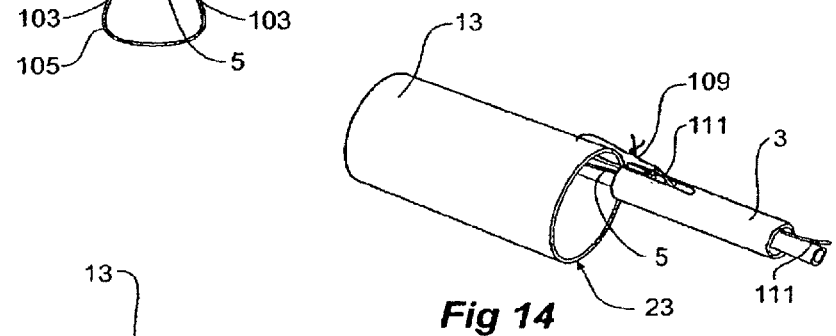
Fig 14
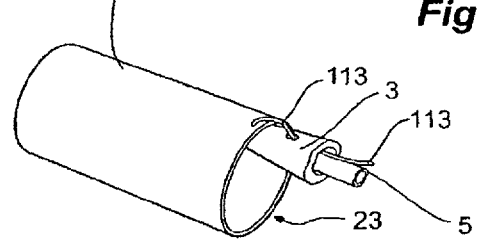
Fig 15

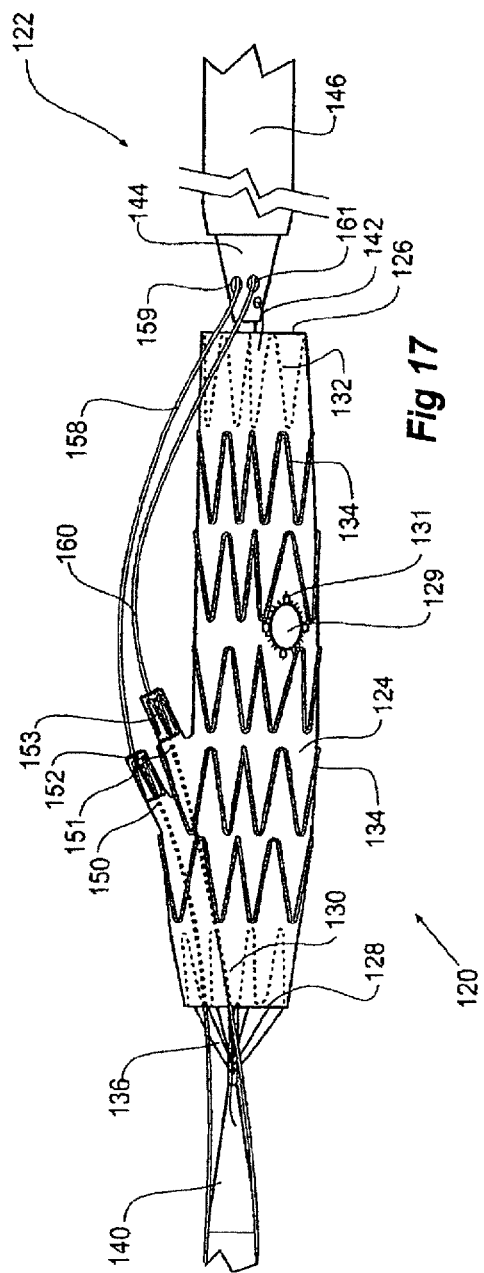

INTRODUCER FOR A SIDE BRANCH DEVICE

CROSS-REFERENCE TO RELATED APPLICATIONS

This application is a divisional of U.S. application Ser. No. 13/181,125, filed on Jul. 12, 2011, now U.S. Pat. No. 9,770,321, which is a divisional of U.S. patent application Ser. No. 11/713,388, filed on Mar. 2, 2007, now U.S. Pat. No. 7,998,186, which claims priority of provisional application Ser. No. 60/778,571, filed Mar. 2, 2006, and is a continuation-in-part of U.S. patent application Ser. No. 10/962,763, filed Oct. 12, 2004, now U.S. Pat. No. 8,012,193, which claims priority to provisional application Ser. No. 60/601,485, filed Aug. 13, 2004 and provisional application Ser. No. 60/510,823, filed Oct. 14, 2003.

TECHNICAL FIELD

This invention relates to a medical device and more particularly to a medical device adapted for deployment of a stem graft within a human or animal body.

BACKGROUND OF THE INVENTION

This invention will be generally discussed in relation to deployment of a stent graft into an iliac artery where it is necessary to extend a side branch from a stent graft into an internal iliac artery but it is to be understood that the invention is not so limited and may relate to any body lumen in which such a deployment is required. One particular application to which the present invention is directed but not restricted to is the deployment of a side arm stent or stent graft into a blind vessel. The term blind vessel is intended to refer to those vessels which because of their configuration can only be approached from a main vessel from which the blind vessel extends.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Stent grafts are used for treatment of vasculature in the human or animal body to bypass or repair a defect in the vasculature. For instance, a stent graft may be used to span an aneurysm which has occurred in or associated with the iliac artery. In many cases, however, such a damaged or defective portion of the vasculature may include a branch vessel such as an internal iliac artery. Bypassing such a branch vessel without providing blood flow into it can cause problems and hence it has been proposed to provide a side branch on a stent graft which when deployed is positioned over the opening to the internal iliac artery and then another stent graft can be deployed through the side branch into the internal iliac artery to provide a blood flow path to the internal iliac artery.

Generally, when deploying an endovascular stent graft into a body lumen, it is possible to obtain access to such a body lumen from each end of the lumen where necessary, thereby facilitating placement of a device in the lumen. The internal iliac artery which extends from the common iliac artery below the aortic bifurcation is for all intents and purposes a blind vessel because there is no practical way of performing an endovascular minimally invasive procedure into that vessel other than by entry from the common iliac artery. The term blind vessel is used herein to describe such a vessel.

There have been proposals to deploy a branched stent graft into the common iliac artery via a femoral artery from a femoral incision with the branched stent graft having a side arm to extend into or at least adjacent the internal iliac artery, however, the use of such devices is very dependent upon favourable layout of the arteries and in many cases, access is extremely difficult. This invention proposes an alternative method for approaching the common iliac artery and a deployment device to enable such a method to be practised.

It is the object of this invention therefore to provide an improved deployment device or at least to provide a physician with a useful alternative.

SUMMARY OF THE INVENTION

In one form therefore, although this may not necessarily be the only or broadest form, the invention is said to reside in an introduction arrangement for a branched stent graft intended for deployment into the lumen of a vessel having a blind vessel extending therefrom; the branched stent graft having a main tubular body having a distal end and a proximal end with a main lumen therethrough, a side arm extending from the main body and having a side arm lumen therethrough and in fluid communication with the main lumen, the introduction arrangement including an introducer, the introducer having a distal end intended to remain outside a patient in use and a proximal end, the proximal end having a nose cone dilator and an arrangement to retain the branched stent graft thereon distally of the nose cone dilator, the branched stent graft being retained on the introducer and a sheath on the introducer extending over the branched stent graft to the nose cone dilator, an indwelling catheter extending from the distal end of the introducer through an introducer lumen in the introducer to the branched stent graft, exiting from the introducer lumen at a distal end of the branched stent graft and entering the distal end of the side arm through the side arm lumen to the main lumen and extending to the proximal end of the branched stent graft, the indwelling catheter having a guide wire extending therethrough, whereby the indwelling catheter and guide wire can be extended beyond the proximal end of the branched stent graft in use after the sheath has been at least partially withdrawn from the branched stent graft.

In one embodiment the branched stent graft comprises a plurality of side arms and a plurality of indwelling catheters, each side arm having a side arm lumen, each respective indwelling catheter extending from the distal end of the introducer through the introducer lumen in the introducer to the branched stent graft, exiting from the introducer lumen at a distal end of the branched stent graft and entering the respective distal end of the side arm through the respective side arm lumen to the main lumen and extending to the proximal end of the branched stent graft.

The means to retain the branched stent graft on the introducer can include trigger wires extending to the distal end of the introducer and release arrangements for separate release of the proximal and distal ends of the stent graft from the introducer.

In an alternative form the invention is said to reside in an introducer device and a stent graft retained thereon, the stent graft comprising a tubular body and a fenestration in the tubular body, an indwelling catheter having a guide wire extending therethrough and associated with the introducer device, the indwelling catheter extending through fenestration and into the stent graft and to the proximal end of the stent graft whereby the guide wire can be advanced beyond the proximal end of the stent graft and introducer device so that it can be snared and a deployment device for a side arm can be deployed over the guide wire, once snared, to enter the fenestration.

The stent graft has a proximal end and a distal end and the indwelling catheter preferably extends outside of the stent graft distally of the fenestration and through the fenestration into the stent graft and towards the proximal end.

The fenestration can include a side arm extending therefrom. The side arm extending from the fenestration can extend inside the stent graft towards either the proximal or distal ends thereof or the side arm extending from the fenestration can extend outside the stent graft towards either the proximal or distal ends thereof.

In an alternative form the invention is said to reside in an introduction arrangement for a fenestrated graft intended for deployment into the lumen of a vessel having a blind vessel extending therefrom; the fenestrated stent graft having a main tubular body having a distal end and a proximal end with a main lumen therethrough, a fenestration in the main body, the introduction arrangement including an introducer, the introducer having a distal end intended to remain outside a patient in use and a proximal end, the proximal end having a nose cone dilator and an arrangement to retain the fenestrated stent graft distally of the nose cone dilator, the fenestrated stent graft being retained on the introducer and a sheath on the introducer extending over the fenestrated stent graft to the nose cone dilator, an indwelling catheter extending from the distal end of the introducer through an introducer lumen in the introducer to the fenestrated stent graft, exiting from the introducer lumen at a distal end of the fenestrated stent graft and entering the fenestration to the main lumen and extending to the proximal end of the fenestrated stent graft, the indwelling catheter having a guide wire extending therethrough, whereby the guide wire can be extended beyond the nose cone dilator in use after the sheath is withdrawn from the fenestrated stent graft.

Preferably the means to retain the fenestrated stent graft on the introducer includes trigger wires extending to the distal end of the introducer and release arrangements for separate release of the proximal and distal ends of the stent graft from the introducer.

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO98/53761 could be used with the present invention and the disclosure of PCT Patent Publication No. WO98/53761 is herewith incorporated in its entirety into this specification.

PCT Patent Publication No. WO99/29262 which became U.S. Pat. No. 6,524,335 and issued on Feb. 25, 2003, entitled "Endoluminal Aortic Stents" discloses a fenestrated prosthesis for placement where there are intersecting arteries. This feature and other features disclosed in PCT Patent Publication No. WO99/29262 could be used with the present invention and the disclosure of PCT Patent Publication No. WO99/29262 is herewith incorporated in its entirety into this specification. As disclosed therein at column 2, lines 18-21, "There may be two or more fenestrations according to the number of intersecting arteries. The or each fenestration may include one or more radiopaque markers define a periphery of the fenestration." As set fourth at column 6 lines 48-59, "There may be more than two fenestrations in the biocompatible graft material tube where there are more than two arteries." FIGS. 1,7, and 9-11 show at least two fenestrations in the graft material.

As shown in U.S. Pat. No. 6,524,335 in at least FIGS. 6-9, the introduction system has a proximal cap 24. At column 5, lines 41-42, the specification states that "The proximal cap 24 covers the top part of the proximal Z-stent." Pat. No. 6,524,335 also discloses a stent extending proximally from the tube of the fenestrated graft material, for example in FIG. 1-3 and at column 4, lines 43-47.

PCT Patent Publication No. WO03/034948 entitled "Prostheses for Curved Lumens" discloses prostheses with arrangements for bending the prosthesis for placement into curved lumens. This feature and other features disclosed in PCT Patent Publication No. WO03/034948 could be used with the present invention and the disclosure of PCT Patent Publication No. WO03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, and Published on Dec. 18, 2003, as US Patent Application Publication No. US-2003-0233140-A1 entitled "Trigger Wires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 could be used with the present invention and the disclosure of U.S. Provisional Patent Application Ser. No. 60/392,682 and U.S. patent application Ser. No. 10/447,406, filed May 29, 2003 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, entitled "Thoracic Deployment Device" disclose introducer devices adapted for deployment of stent grafts particularly in the thoracic arch. This feature and other features disclosed in U.S. Provisional Patent Application Ser. No. 60/392,667 and U.S. patent application Ser. No. 10/609,846, filed Jun. 30, 2003 could be used with the present invention and the disclosure of U.S.

Provisional Patent Application Ser. No. 60/392,667 and U.S. patent application Ser. No. 10/609,846, filed Jun. 30, 2003 are herewith incorporated in their entirety into this specification.

U.S. Provisional Patent Application Ser. No. 60/392,599, filed Jun. 28, 2002, and U.S. patent application Ser. No. 10/609,835, filed Jun. 30, 2003, entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No. 60/392,599 and U.S. patent application Ser. No. 10/609,835, filed Jun. 30, 2003 could be used with the present invention, and the disclosure are herewith incorporated in their entirety into this specification.

U.S. Provisional Patent Application Ser. No. 60/391,737, filed Jun. 26, 2002, U.S. patent application Ser. No. 10/602,930, filed Jun. 24, 2003, and PCT Patent Publication Number WO 2004/002365 entitled "Stent-Graft Fastening" disclose arrangements for fastening stents onto grafts particularly for exposed stents. This feature and other features disclosed in U.S. Provisional Patent Application No. 60/391,737, U.S. patent application Ser. No. 10/602,930, and PCT Patent Publication Number WO 2004/002365 could be used with the present invention and the disclosure of U.S. Provisional Patent Application Ser. No. 60/391,73, U.S. patent application Ser. No. 10/602,930, and PCT Patent Publication Number WO 2004/002365 are herewith incorporated in its entirety into this specification.

U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 entitled "Asymmetric Stern Graft Attachment" disclose retention arrangements for retaining onto and releasing prostheses from introducer devices. This feature and other features disclosed in U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 could be used with the present invention and the disclosure of U.S. Provisional Patent Application Ser. No. 60/405,367, filed Aug. 23, 2002, U.S. patent application Ser. No. 10/647,642, filed Aug. 25, 2003, and PCT Patent Publication No. WO 2004/017868 are herewith incorporated in its entirety into this specification.

U.S. patent application Ser. No. 10/322,862, filed Dec. 18, 2002 and published as Publication No. US2003-0120332, and PCT Patent Publication No. WO03/053287 entitled "Stent Graft With improved Adhesion" disclose arrangements on stent grafts for enhancing the adhesion of such stent grafts into walls of vessels in which they are deployed. This feature and other features disclosed in U.S. patent application Ser. No. 10/322,862, filed Dec. 18, 2002 and published as Publication No. US2003-0120332, and PCT Patent Publication No. WO03/053287 could be used with the present invention and the disclosure of U.S. patent application Ser. No. 10/322,862, filed Dec. 18, 2002 and published as Publication No. US2003-0120332, and PCT Patent Publication No. WO03/053287 are herewith incorporated in its entirety into this specification.

U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 entitled "Composite Prostheses" discloses prostheses or stent grafts suitable for endoluminal deployment. These prostheses and other features disclosed in U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867, could be used with the present invention and the disclosure of U.S. Provisional Patent Application Ser. No. 60/405,769, filed Aug. 23, 2002, U.S. patent application Ser. No. 10/645,095, filed Aug. 23, 2003, and PCT Patent Publication Number WO 2004/017867 are herewith incorporated in its entirety into this specification.

BRIEF DESCRIPTION OF THE DRAWING

This then generally describes the invention but to assist with the understanding, reference will now be made to the accompanying drawings which show a preferred embodiment of the invention and a method by which the preferred embodiment of the invention may be used to deploy a stent graft into the internal iliac artery.

In the drawings;

FIG. 7 shows a schematic view of a deployment device with a stent graft mounted thereon according to one embodiment of the invention;

FIG. 8 shows a schematic view of a deployment device with a stent graft mounted thereon according to an alternative embodiment of the invention;

FIG. 9 shows a further schematic view of the deployment device shown in FIG. 8;

FIG. 11 shows a schematic view of a deployment device with a stent graft mounted thereon according to a further embodiment of the invention;

FIG. 12 shows a side view of one method of proximal retention suitable for the present invention;

FIG. 13 shows a cross sectional view of the arrangement shown in FIG. 12;

FIG. 14 shows a side view of one method of distal retention suitable for the present invention;

FIG. 15 shows a side view of an alternative method of distal retention suitable for the present invention; FIG. 17 shows a part view of an alternative embodiment of deployment device with a stent graft mounted thereon.

DETAILED DESCRIPTION

Figure 1:
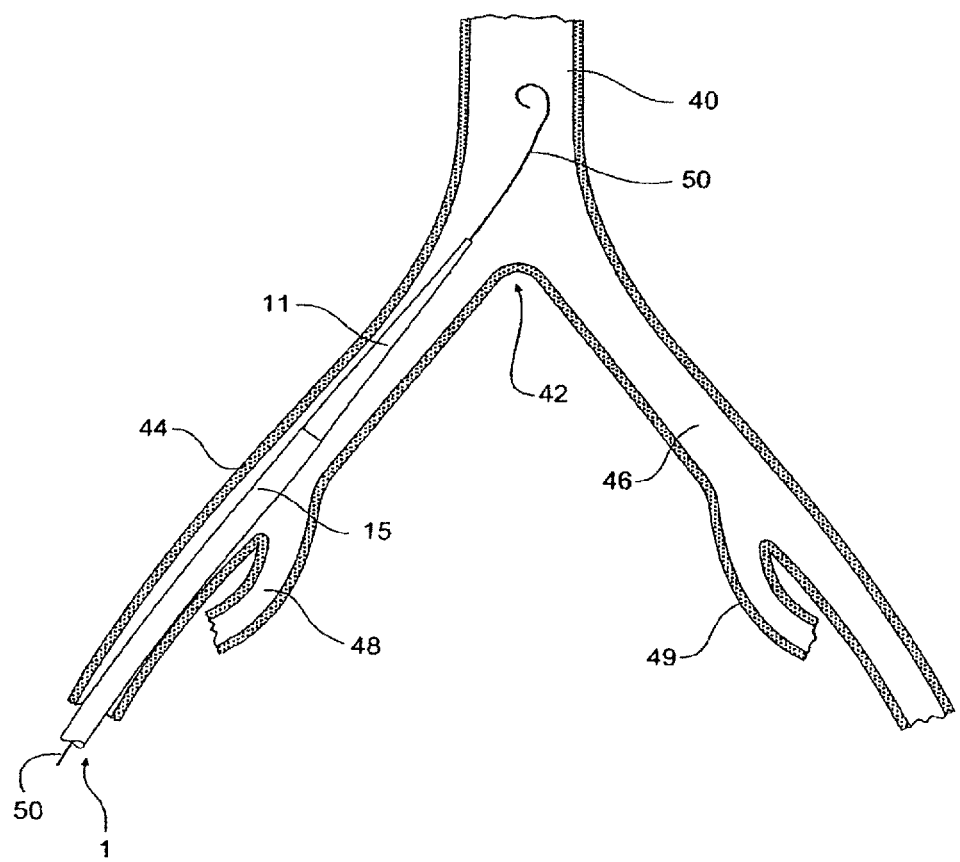
FIGS. 1 to 6 show the various stages of deployment of a stent graft on a deployment device into an iliac artery according to one embodiment of the present invention.

Now looking first at FIG. 7, a deployment device with a stent graft mounted onto it according to one embodiment of the present invention is shown schematically.

The deployment device generally shown as 1 has an introducer catheter 3 extending over a guide wire catheter 5. The guide wire catheter 5 extends from the distal end 7 of the introducer 1 to and through the nose cone dilator 11. A branched stent graft 13 is retained at its proximal end 6 by a retention arrangement (see FIGS. 12 and 13 for one example of a proximal retention arrangement) onto the deployment device immediately distal of the nose cone dilator 11. The branched stent graft 13 is retained at its distal end 23 by another retention arrangement (see FIGS. 14 and 15 for examples of distal retention arrangements) onto the deployment device. A sheath 15 operated by a sheath manipulator 17 is mounted on the introducer catheter 3 and in the ready to deploy position the sheath 15 extends over the branched stent graft 13 to the nose cone dilator 11. As illustrated in FIG. 7, however, the sheath 15 is withdrawn so that the branched stent graft is exposed to show detail of the assembly. A handle 19 at the distal end of the introducer catheter 3 enables manipulation of the introducer 1. An indwelling catheter 21 enters a lumen (not shown) of the introducer catheter 3 at the handle 19 and exits from the introducer catheter 3 at the distal end 23 of the branched stent graft 13.

The branched stent graft 13 has a substantially tubular body with a main lumen through the main tubular body and a side lumen through the branch 25. The indwelling catheter 21 enters the lumen of the branch 25 from its distal end 26 and hence it passes outside the main tubular body of the branched stent graft before it enters the branch lumen. The indwelling catheter 21 then terminates within the stem graft 13 adjacent to the nose cone dilator 11.

Within the indwelling catheter 21, there is a guide wire 29. This guide wire 29 can be pushed through the indwelling catheter so that it extends beyond the tip 31 of the nose cone dilator after at least partial release of the proximal end of the stent graft so that it can be snared as will be discussed in relation to FIGS. 1 to 6 showing one embodiment of the stent graft placement procedure. Preferably the tip 32 of the indwelling catheter is tapered around the guide wire 29 to prevent blood loss through the indwelling catheter. The at least partial release of the proximal end of the stent graft may be achieved by withdrawal of the sheath 15 while still using a trigger wire retention arrangement as is discussed in relation to FIGS. 12 and 13 below to retain the proximal end of the stent graft.

Now looking at FIGS. 1 to 6, it will be seen that there is schematically illustrated a series of arteries within the human body, although as discussed earlier, the invention is not restricted to this particular application.

A descending aorta 40 extends down to an aortic bifurcation 42 from which extend common iliac arteries 44 and 46. From each of the common iliac arteries an internal iliac artery 48 and 49, respectively, extends. As discussed earlier, the internal iliac arteries 48 and 49 cannot be practically accessed from their distal ends remote from the junction with the common iliac artery.

As shown in FIG. 1, a guide wire 50 for the deployment device 1 has been extended into a femoral artery via a femoral incision (not shown) and extended up beyond the aortic bifurcation 42 to the aorta 40. The deployment device 1 has then been deployed over the guide wire with the nose cone dilator 11 extending nearly up to the aortic bifurcation. At this stage, the sheath 15 on the deployment device extends up to the nose cone dilator 11.

Figure 2:
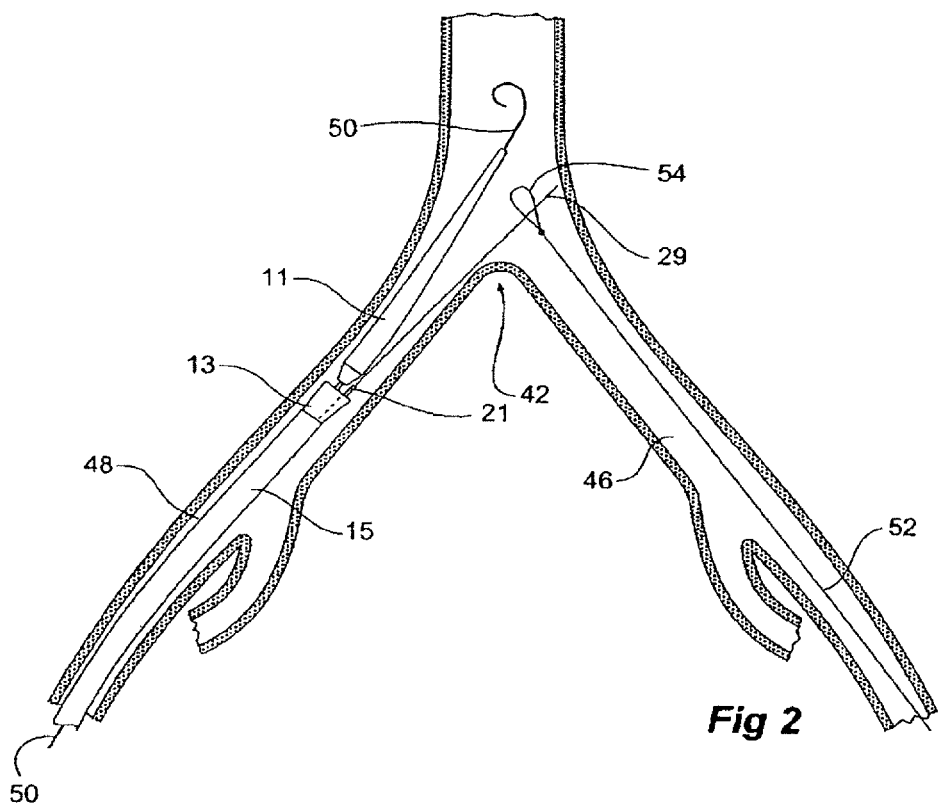

As can be seen in FIG. 2, the sheath 15 has been withdrawn slightly to expose the proximal end of the stent graft 13 and the guide wire 29 in the indwelling catheter 21 has been advanced until it reaches the aortic bifurcation 42 and has been extended further so that it extends up beyond the aortic bifurcation 42 but only a short distance up the aorta 40. A snare catheter 52 has been deployed via the contra-lateral iliac artery 46 and by suitable radiographic techniques the loop 54 of the snare catheter 52 is used to catch the guide wire 29.

Figure 3:
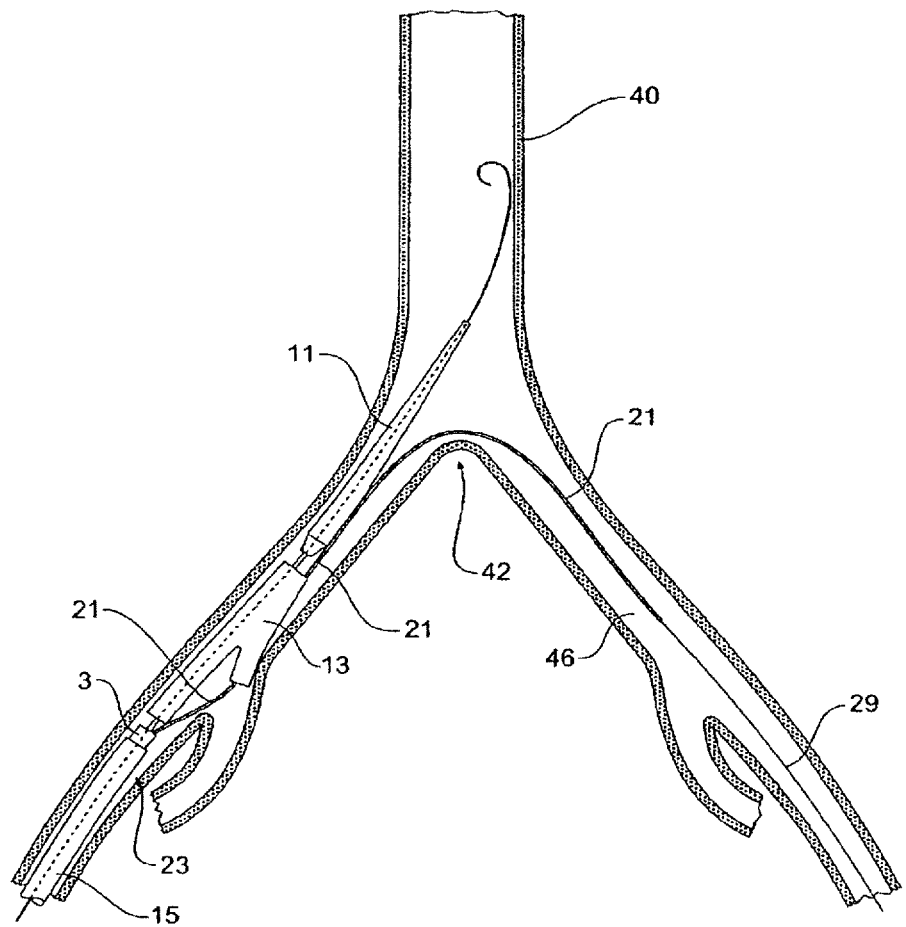

As shown in FIG. 3, the guide wire 29 has been withdrawn through the contra-lateral iliac artery 46 and the indwelling catheter 21 has been advanced over the guide wire so that it extends over the aortic bifurcation 42 and down the contra-lateral iliac artery 46. To assist this process, the sheath 15 has been withdrawn to the distal end 23 of the branched stent graft 13 so that it is just distal of the proximal end of the introducer catheter 3. At this stage the branched stent graft 13 is partially freed but is still retained by retention arrangements (not shown) at the proximal and distal ends of the branched stent graft and is hence in an unexpanded or not fully expanded condition. There may be diameter-reducing ties (not shown) to restrict the amount of expansion.

Figure 4:
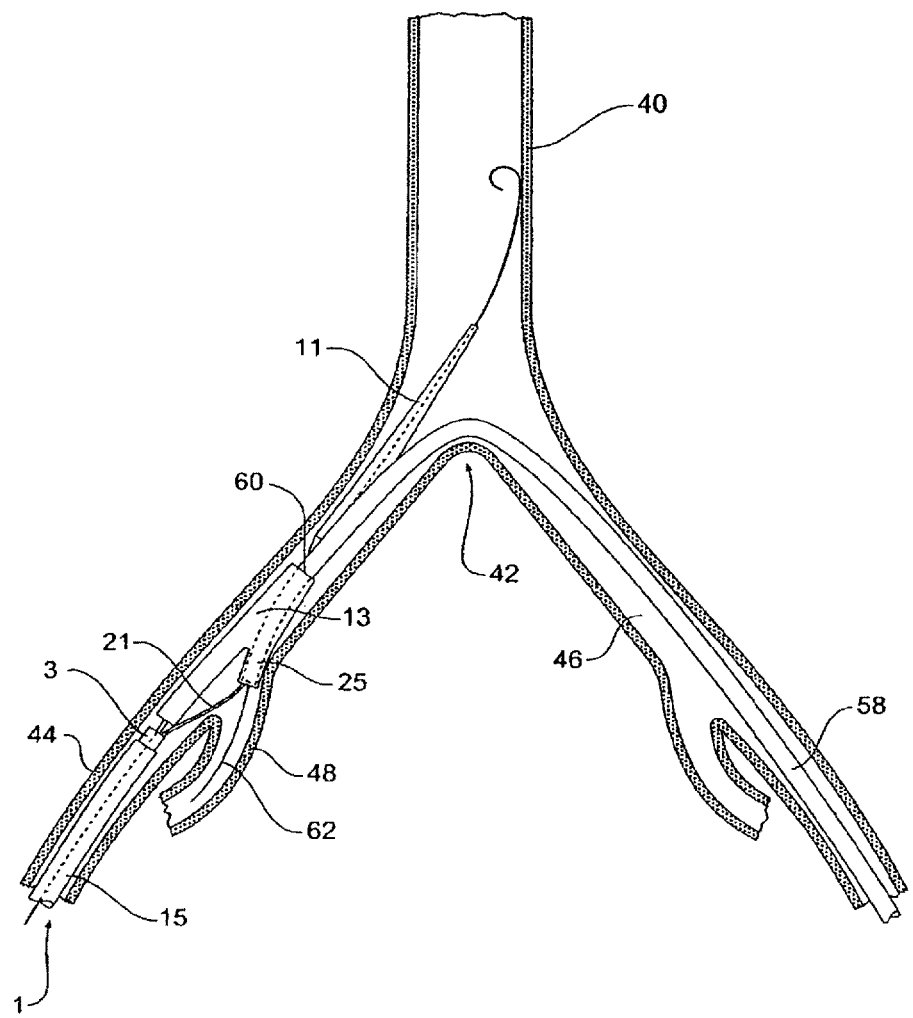

FIG. 4 shows the next stage of the process where a sheath 58 of a suitable size has been advanced over the guide wire 29 via the contralateral artery so that it enters the proximal end 60 of the branched stent graft 13. At this stage, the indwelling catheter 21 and guide wire 29 still extend down the iliac artery 44 and into the lumen of the introducer catheter 3 of the deployment device 1 so that the sheath 58 can be manipulated to successfully enter the proximal end of the branched stent graft so that it extends towards and into the branch 25 on the stent graft 13. At this stage, the indwelling guide wire 29 can be withdrawn either from the contra-lateral iliac artery 46 or from the iliac artery 44, but the indwelling catheter can only be withdrawn from the iliac artery 44. Another guide wire 62 can then be introduced via the sheath 58. This guide wire 62 can then be manipulated so that it enters the internal iliac artery 48.

Figure 5:
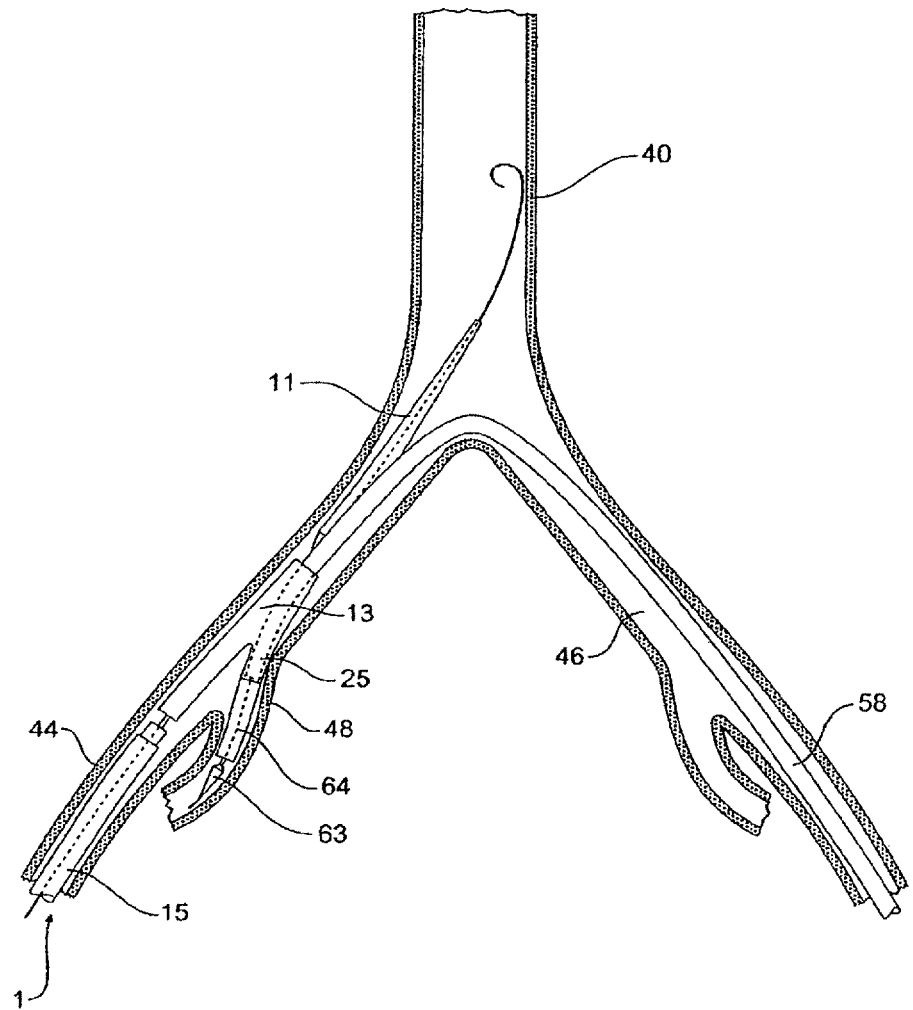

As shown in FIG. 5, a further deployment device 63 can then be introduced via the sheath 58 from the contra-lateral iliac artery 46 to extend out of the distal end of the branch 25 of the branched stent graft 13 so that a leg extension 64 can be deployed to extend from the branch 25 of the branched stent graft 13. The leg extension 64 can for instance be a balloon expandable stent or stent graft carried on a balloon catheter, or a self-expanding stent.

Figure 6:
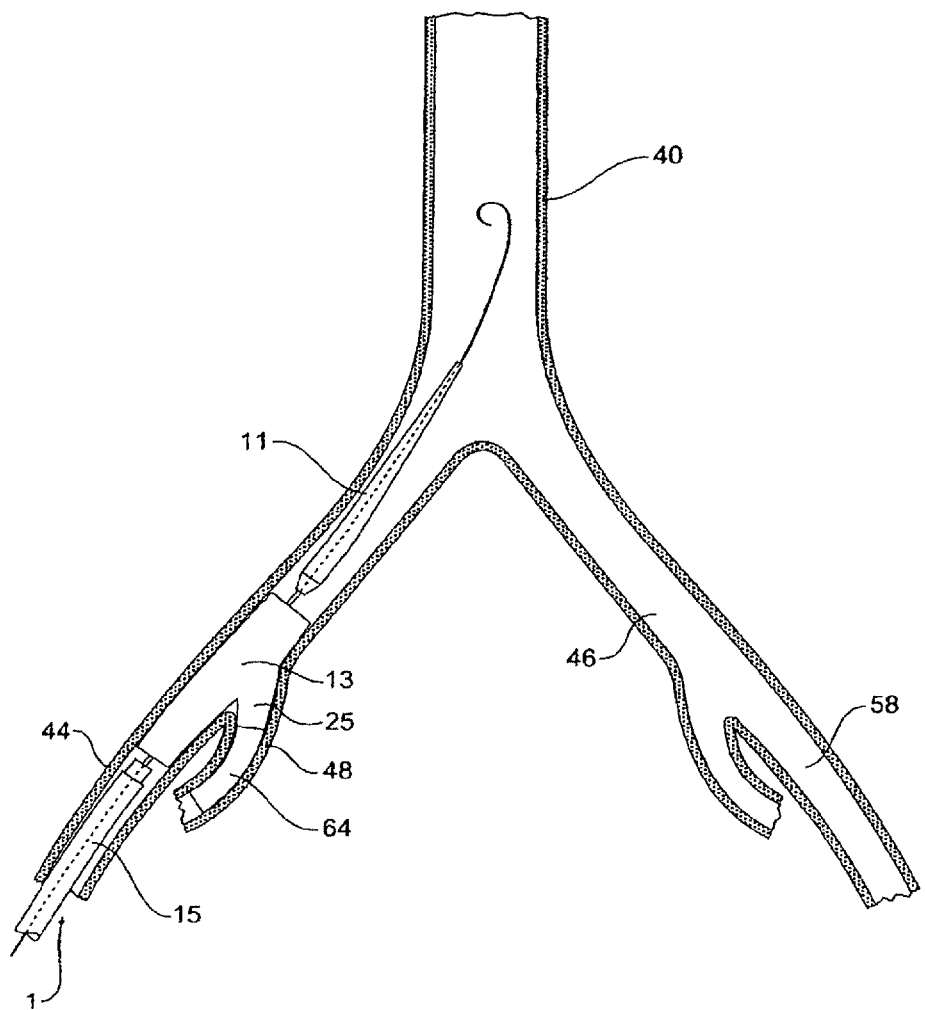

As shown in FIG. 6, the sheath 58 from the contra-lateral iliac artery 46 can then be withdrawn and the release mechanisms at each end of the stent graft 13 can be released and the leg extension 64 released or expanded so that the branched stent graft with leg extension is then deployed in the common iliac artery.

The deployment device 1 can then be withdrawn although in some situations it may be desirable to leave the sheath 15 in position so that further deployment of a stent graft into the aorta such as a bifurcated stent graft can be achieved through the sheath 15.

In summary therefore, the steps in the graft placement procedure accordingly using the device of the present invention may be as follows:

1. Deploy a deployment device into a femoral artery via a femoral incision and extend the deployment device up to the aortic bifurcation.

2. Advance an indwelling guide wire through the indwelling catheter beyond the nose cone dilator of the deployment device.

3. Introduce a snare catheter into the contra-lateral iliac artery via a femoral route and snare the indwelling guide wire.

4. Withdraw the indwelling guide wire through the contra-lateral iliac artery.

5. Withdraw the main sheath to expose the branched stent graft but still have the branched stent graft retained at each of its ends.

6. Advance a catheter over the indwelling guide wire until it enters the proximal end of the stent graft.

7. Deploy an auxiliary sheath over the indwelling guide wire up the contra-lateral iliac artery and into the branched stent graft via the proximal end of the branched stent graft.

8. Advance the auxiliary sheath into the short leg of the branched stent graft via the indwelling catheter guide wire or another guide wire which has been deployed through the sheath which has been placed via the contra-lateral iliac artery.

9. Remove the indwelling catheter and indwelling guide wire.

10. Advance a guide wire through the auxiliary sheath via the contra-lateral iliac artery and manipulate it into the internal iliac artery. At this stage, it may be necessary to withdraw the deployment device or rotate it slightly to guide the branch of the branched stent graft towards the internal iliac artery.

11. Advance a short leg introducer with a leg stent graft over the guide wire in the contra-lateral iliac artery and through the auxiliary sheath and into the internal iliac artery.

12. Release the proximal distal ends of the branched stent graft

13. Release the leg stent graft from the short leg introducer or balloon expand the leg stent graft.

14. Withdraw the contra-lateral iliac artery auxiliary sheath, introducer and guide wire.

15. Withdraw the main introducer.

As discussed earlier it may be necessary or desirable to leave the sheath of the main introducer and/or the main guide wire to enable deployment of further stent grafts within the aorta and aortic bifurcation.

Now looking at FIGS. 8 and 9, an introducer with a stent graft mounted onto it according to an alternative embodiment of the present invention is shown schematically. The same reference numerals are used for corresponding features to those of FIG. 7.

The introducer generally shown as 1 has an introducer catheter 3 extending over a guide wire catheter 5. The guide wire catheter 5 extends from the distal end 7 of the introducer 1 to immediately distal of the nose cone dilator 11 which is at the proximal end 9 of the introducer. A fenestrated stent graft 70 is retained by a retention arrangement (not shown) onto the introducer immediately distal of the nose cone dilator 11. A sheath 15 operated by a sheath manipulator 17 is mounted on the introducer catheter 3 and in the ready to deploy position the sheath 15 extends over the stent graft 70 to the nose cone dilator 11. As illustrated in FIGS. 8 and 9, however, the sheath 15 is withdrawn so that the stent graft is exposed to show detail of the assembly. A handle 19 at the distal end of the introducer catheter 3 enables manipulation of the introducer 1. An indwelling catheter 21 enters a lumen (not shown) of the introducer catheter 3 at the handle 19 and exits from the introducer catheter at the distal end 23 of the stent graft 70.

The stent graft 70 has a substantially tubular body with a main lumen through the main tubular body and a fenestration 71. The indwelling catheter 21 enters the fenestration 71 from outside the stent graft and hence it passes outside the main tubular body of the stent graft at the distal end thereof, before it enters fenestration. The indwelling catheter then passes through the main lumen of the stent graft to its proximal end and terminates within the stent graft 70 or adjacent to the nose cone dilator 11.

Within the indwelling catheter 21, there is a guide wire 29. This guide wire 29 can be pushed through the indwelling catheter so that it extends beyond the tip 31 of the nose cone dilator 11 so that it can be snared as discussed in relation to FIGS. 1 to 6 showing a stent graft placement procedure. Preferably the tip 32 of the indwelling catheter is tapered around the guide wire 29 to prevent blood loss through the indwelling catheter.

Figure 10:
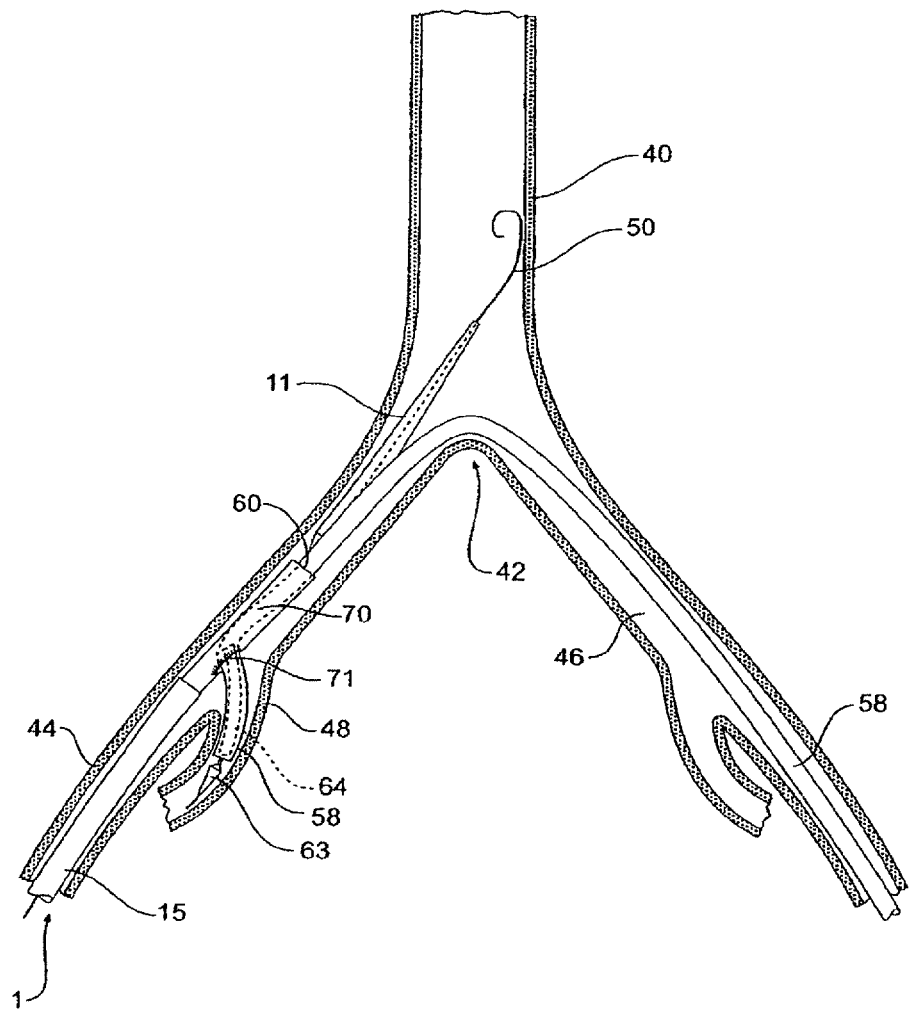
FIG. 10 shows a stage of deployment of the stent graft as shown in FIGS. 8 and 9 corresponding to the stage of deployment shown in FIG. 5 above.

FIG. 10 shows a stage of deployment of the stent graft as shown in FIGS. 8 and 9 corresponding to the stage of deployment shown in FIG. 5 above. The same reference numerals are used for corresponding features to those of FIGS. 1 to 6.

Prior to the stage shown in FIG. 10 a guide wire 50 for the deployment device 1 has been extended into a femoral artery via a femoral incision (not shown) and extended up beyond the aortic bifurcation 42 into the aorta 40. An introducer 1 has then been deployed over the guide wire with the nose cone dilator 11 extending nearly up to the aortic bifurcation. At this stage, the sheath 15 on the deployment device extends up to the nose cone dilator but has been withdrawn slightly to expose the proximal end of the stent graft 70. At this stage the proximal end of the branched stent graft 13 is partially freed but is still retained by a proximal retention arrangement (not shown). Next a guide wire from an indwelling catheter (not shown in FIG. 10) has been extended so that it extends up beyond the aortic bifurcation but only a short distance up the aorta 40. A snare catheter has been deployed via the contra-lateral iliac artery 46 and by suitable radiographic techniques the loop of the snare catheter has been used to catch the guide wire. The guide wire has then been withdrawn through the contra-lateral iliac artery 46 and the indwelling catheter has been advanced over the guide wire so that it extends over the aortic bifurcation 42 and down the contra-lateral iliac artery 46. To assist this process, the sheath 15 has been withdrawn to just distal of the fenestration 25 and still covering the distal end 23 of the stent graft 70. At this stage the stent graft 13 is partially freed but is still retained by a retention arrangements at the proximal end 60 of the stent graft and by the sheath at the distal end. The exposed portion of the stent graft between the proximal end and the fenestration can expand although there may be diameter-reducing ties (not shown) to restrict the amount of expansion. Next a sheath 58 of a suitable size has been advanced over the guide wire 29 so that it enters the proximal end 60 of the branched stent graft 70. At this stage, the indwelling catheter and guide wire 29 still extends down the iliac artery 44 on the introducer 1 so that the sheath 58 can be manipulated to successfully enter the proximal end of the branched stent graft 60 so that it extends towards and into the fenestration 71 on the stent graft 70. At this stage, the indwelling guide wire 19 can be withdrawn, either from the contra-lateral iliac artery 46, but the indwelling catheter may only be removed from the iliac artery 44 and another guide wire 62 introduced via the sheath 58. This guide wire 62 can then be manipulated so that it enters the internal iliac artery 48.

As shown in FIG. 10, a further deployment device 63 has then been introduced via the sheath 58 from the contra-lateral iliac artery 46 to extend out of the fenestration 71 of the stent graft 70. The further deployment device 63 carries a leg extension 64. The leg extension 64 can be deployed to extend from the fenestration 71 of the stent graft 70. The leg extension 64 can be a covered balloon expandable stent for instance, which is carried on a balloon of a balloon catheter in the deployment device so that it can be deployed and expanded with its proximal end retained in the fenestration and extending into the internal iliac artery 48.

Now looking at FIG. 11, an introducer with a stent graft mounted onto it according to an alternative embodiment of the present invention is shown schematically.

In this embodiment the stent graft 90 has a fenestration 94 in the wall of the stent graft 90 and an internal leg extension 92 extending inwardly and toward the proximal end 74 of the stent graft 90 from the fenestration 94. The indwelling catheter 80 extends into the fenestration 94 and into the internal leg extension 92 and toward the proximal end 74 of the stent graft 90 and terminates within the stent graft 90 or adjacent to the nose cone dilator 11.

FIGS. 8 to 11 show various embodiments of the present invention in a stylised manner. It should be noted that the configuration with the main sheath withdrawn completely off the stent graft but with the indwelling catheter and guide wire in its initial position would not occur in practice.

FIG. 12 shows a side view of one method of proximal retention suitable for the present invention and FIG. 13 shows a cross sectional view of the arrangement shown in FIG. 12. The same reference numerals are used for corresponding features to those of FIG. 7 for corresponding items.

The guide wire catheter 5 extends to and through a nose cone dilator 11. Around the proximal end of the guide wire catheter is a trigger wire catheter 8 and the proximal end of the stent graft 13 is retained onto the trigger wire catheter 8 just distal of the nose cone dilator. Retention is by a pair of loops of suture material 101 each of which is engaged with a trigger wire 103 which extends from an aperture 104 in the trigger wire catheter 8. The loops 101 are placed so that there is formed a smaller 105 and larger fold 107 of the stent graft 13 at its proximal end. The indwelling guide wire when advanced from its position at deployment passes through the region defined by the larger fold 107 and therefore when the sheath 58 (see FIG. 4) has been advanced over the guide wire back into the proximal end of the stent graft then it can more easily enter the lumen of the stent graft. Although two fastenings to the trigger wires have been shown further trigger wires such as three or four may be used.

FIG. 14 shows a side view of one method of distal retention suitable for the present invention. The same reference numerals are used for corresponding features to those of FIG. 7 for corresponding items. In this embodiment the distal end 23 of the stent graft 13 is retained onto the proximal end of the deployment catheter by means of a suture loop 109 engaged into the stent graft 13 and a loop of trigger wire 111 extending from the deployment catheter 3. Removal of the trigger wire 111 when required will release the distal end 23 of the stent graft 13.

FIG. 15 shows a side view of an alternative method of distal retention suitable for the present invention. The same reference numerals are used for corresponding features to those of FIG. 7 for corresponding items. In this embodiment the distal end 23 of the stent graft 13 is retained directly onto the deployment catheter 3 by means a loop of trigger wire 113 extending from the deployment catheter 3 and passing through a portion of the stent graft 13. Removal of the trigger wire 113 when required will release the distal end 23 of the stent graft 13.

Figure 16:
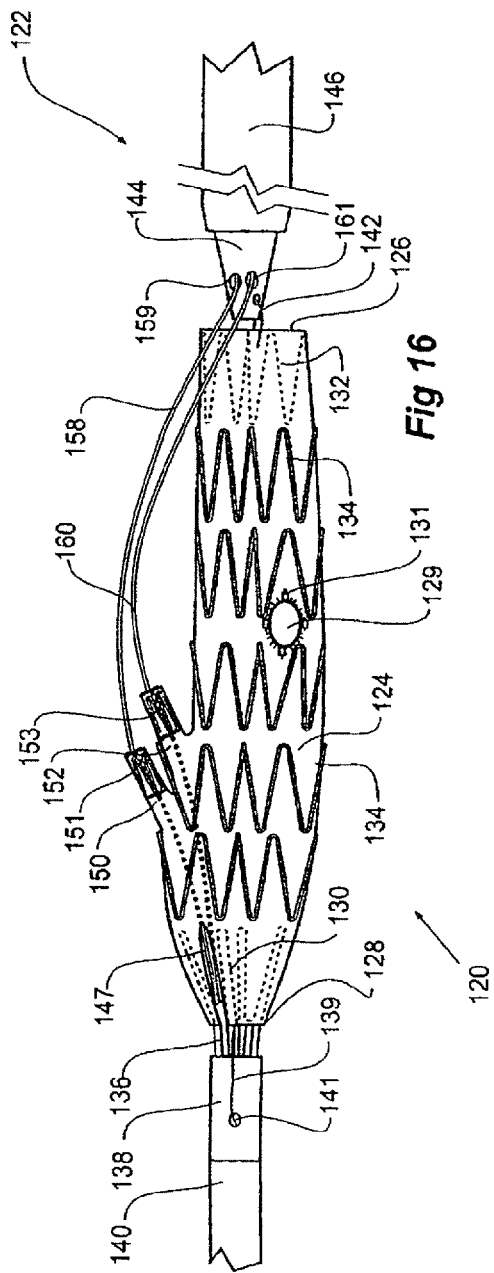
FIG. 16 shows a part view of an alternative embodiment of deployment device with a stent graft mounted thereon.

FIG. 16 shows a part view of an alternative embodiment of deployment device with a stent graft mounted thereon. In this embodiment the stent graft is of a type adapted for deployment into the aorta in the region of the coeliac, mesenteric and renal arteries for treatment of aneurysmal disease in that region. The stent graft 120 which is mounted onto the deployment device 122 comprises a tubular body 124 with a proximal end 128 and a distal end 126. There are internal Gianturco style self expanding Z stents 130 and 132 fastened to the tubular body 124 at the proximal and distal ends respectively and external Gianturco style self expanding Z stents 134 fastened to the tubular body 124 between them. Extending from the proximal end 128 and fastened to the proximal end 128 of the tubular body 124 is an exposed Gianturco style self expanding Z stent 136. Also present on the stent graft 120 is a fenestration 129 with radiopaque markers 131 defining its periphery. The fenestration 129 is used for access to one of the renal arteries. There may be another fenestration for access to the other renal artery. The stent graft 120 has a proximal scallop 147.

The proximal end of the stent graft 120 is retained on to the delivery device 122 by the exposed Gianturco style self expanding Z stent 136 being retained within a capsule 138 on a nose cone dilator 140 at the proximal end of the delivery device 122. A trigger wire 139 extends out from the tubular body 124 and passes into an aperture 141 in the capsule 138 and engages into a bend (not shown) in the exposed stent 136 so that the capsule cannot be withdrawn until the trigger wire has first been removed. The distal end of the stent graft 120 is retained on to the delivery device 122 by a trigger wire 142 which passes through a lumen (not shown) in a pusher catheter 144 of the delivery device and into the material of the tubular body 124. Possible distal retention arrangements are shown in FIGS. 14 and 15. In the ready to deliver configuration the sheath 146 would extend forward to the nose cone dilator 140 but is shown in the retracted condition to allow visualisation of the stent graft 120.

Extending from the stent graft towards the distal end 126 is a first side branch 150 which is intended for placement of a side branch extension for the coeliac artery and a second side branch 152 which is intended for placement of a side branch extension for the superior mesenteric artery. The first side branch 150 has an Gianturco style self expanding Z stent 151 to act as a sealing stent when the leg extension is deployed therein and the second side branch 152 has a Gianturco style self expanding Z stent 153 to act as a sealing stent when the leg extension is deployed therein. The first side branch 150 has a first indwelling catheter 158 which passes through a lumen (not shown) in the pusher catheter 144 of the delivery device, extends out of an aperture 159 in the proximal end of the pusher catheter 144 and passes outside of the distal end 126 of the stent graft 120 before entering the first side arm 150 and terminating within the proximal end 128 of the stent graft 122 adjacent to the scallop 147 or adjacent to the nose cone dilator 140. The second side branch 152 has a second indwelling catheter 160 which passes through a lumen (not shown) in the pusher catheter 144 of the delivery device, extends out of an aperture 161 in the proximal end of the pusher catheter 144 and passes outside of the distal end 126 of the stent graft 120 before entering the second side arm 152 and terminating within the proximal end 128 of the stent graft 122 adjacent to the scallop 147 or adjacent to the nose cone dilator 140.

Within each of the indwelling catheters 158 and 160 there are guide wires (not shown). These guide wires can be pushed through the indwelling catheter so that they extend through the scallop 147 and beyond the tip (not shown) of the nose cone dilator 140 after at least partial release of the proximal end of the stent graft 128 so that it can be snared as was be discussed above. The at least partial release of the proximal end of the stent graft 128 may be achieved by withdrawal of the sheath 146 to at least distal of the second side arm 152.

FIG. 17 shows a part view of a still further alternative embodiment of deployment device with a stent graft mounted thereon. The device is similar to the device shown in FIG. 16 and the same reference numerals are used for corresponding features. In this embodiment the stent graft is of a type adapted for deployment into the aorta in the region of the coeliac, mesenteric and renal arteries for treatment of aneurysmal disease in that region. The stent graft 120 which is mounted onto the deployment device 122 comprises a tubular body 124 with a proximal end 128 and a distal end 126. There are internal Gianturco style self expanding Z stents 130 and 132 fastened to the tubular body 124 at the proximal and distal ends respectively and external Gianturco style self expanding Z stents 134 fastened to the tubular body 124 between them. Extending from the proximal end 128 and fastened to the proximal end 128 of the tubular body 124 is an exposed Gianturco style self expanding Z stent 136. Also present on the stent graft 120 is a fenestration 129 with radiopaque markers 131 defining its periphery. The fenestration 129 is used for access to one of the renal arteries. There may be another fenestration for access to the other renal artery.

The proximal end of the stent graft 120 is retained on to the delivery device 122 by the exposed Gianturco style self expanding Z stent 136 being retained by a trigger wire system to the deployment device just distal of the nose cone dilator 140. US Patent Application Publication No. US-2003-0233140-A1 entitled "Trigger Wires" disclose release wire systems for retention and release of stent grafts retained on introducer devices. This teaching is incorporated in its entirety into this specification.

Extending from the stent graft towards the distal end 126 is a first side branch 150 which is intended for placement of a side branch extension for the coeliac artery and a second side branch 152 which is intended for placement of a side branch extension for the superior mesenteric artery. The first side branch 150 has an Gianturco style self expanding Z stent 151 to act as a sealing stent when the leg extension is deployed therein and the second side branch 152 has a Gianturco style self expanding Z stent 153 to act as a sealing stent when the leg extension is deployed therein. The first side branch 150 has a first indwelling catheter 158 which passes through a lumen (not shown) in the pusher catheter 144 of the delivery device, extends out of an aperture 159 in the proximal end of the pusher catheter 144 and passes outside of the distal end 126 of the stent graft 120 before entering the first side arm 150 and terminating adjacent the nose cone dilator. The second side branch 152 has a second indwelling catheter 160 which passes through a lumen (not shown) in the pusher catheter 144 of the delivery device, extends out of an aperture 161 in the proximal end of the pusher catheter 144 and passes outside of the distal end 126 of the stent graft 120 before entering the second side arm 152 and terminating adjacent the nose cone dilator 140.

Within each of the indwelling catheters 158 and 160 there are guide wires (not shown). These guide wires can be pushed through the indwelling catheter so that they extend beyond the tip (not shown) of the nose cone dilator 140 after at least partial release of the proximal end of the stent graft 128 so that it can be snared as was be discussed above. The at least partial release of the proximal end of the stent graft 128 may be achieved by withdrawal of the sheath 146 to at least distal of the second side arm 152.

Throughout this specification various indications have been given as to the scope of this invention but the invention is not limited to any one of these but may reside in two or more of these combined together. The examples are given for illustration only and not for limitation.

Throughout this specification and the claims that follow, unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft introduction arrangement in combination with a fenestrated stent graft,
the fenestrated stent graft comprising a main tubular body, a distal end, a proximal end, a main lumen therethrough, at least one fenestration in the main body between the distal and the proximal end of the main body, and an internal side arm extending from the at least one fenestration and into the main lumen;
the introduction arrangement including an introducer, the introducer comprising a distal end intended to remain outside a patient in use and a proximal end, the proximal end of the introducer comprising a nose cone dilator and retention arrangement to retain the fenestrated stent graft thereon distally of the nose cone dilator, the fenestrated stent graft being retained on the introducer and a sheath on the introducer extending over the fenestrated stent graft to the nose cone dilator,
an indwelling catheter for each of said at least one fenestration, each indwelling catheter extending from the distal end of the introducer through an introducer lumen in the introducer to the fenestrated stent graft, the each indwelling catheter then exiting from the introducer lumen at a distal end of the fenestrated stent graft, the each indwelling catheter then extending outside and along the main tubular body, then entering the at least one the respective fenestration, extending through the internal side arm, and extending into the main lumen and toward the proximal end of the fenestrated stent graft, each the indwelling catheter configured to receive a guide wire extending therethrough,
whereby the indwelling catheter and the guide wire can be extended beyond the proximal end of the fenestrated stent graft in use after the sheath has been at least partially withdrawn from the fenestrated stent graft.

2. The stent graft introduction arrangement in combination with the fenestrated stent graft of claim 1, where the fenestrated stent graft comprises a plurality of.

3. The stent graft introduction arrangement in combination with the fenestrated stent graft of claim 1, wherein the indwelling catheter terminates within the main lumen.

4. The stent graft introduction arrangement in combination with the fenestrated stent graft of claim 1, wherein the indwelling catheter is adjacent the nose cone dilator.

5. The stent graft introduction arrangement in combination with the fenestrated stent graft of claim 1, where the retention arrangement to retain the fenestrated stent graft on the introducer comprises trigger wires extending to the distal end of the introducer and release arrangements for separate release of the proximal and distal ends of the stent graft from the introducer.

6. The stent graft introduction arrangement in combination with the fenestrated stent graft of claim 1, where the fenestrated stent graft comprises a proximally extending exposed stent and the nose cone dilator comprises a distally facing capsule, the retention arrangement comprising the exposed stent being received into the distally facing capsule during deployment of the stent graft and release of the retention arrangement comprises advancing the nose cone dilator to release the exposed stent from the nose cone dilator.

7. The stent graft introduction arrangement in combination with the fenestrated stent graft of claim 1, where the fenestrated stent graft comprises a proximally extending exposed stent, and a trigger wire system just distal of the nose cone dilator comprises the retention arrangement for the proximal end of the stent graft.

8. The stent graft introduction arrangement in combination with the fenestrated stent graft of claim 1, where the guide wire can be extended beyond the proximal end of the fenestrated stent graft in use after the sheath has been at least partially withdrawn from the fenestrated stent graft and before the retention arrangement to retain the fenestrated stent graft thereon distally of the nose cone dilator has been released.

9. The stent graft introduction arrangement in combination with the fenestrated stent graft of claim 1, wherein the internal side arm is configured to receive a leg extension.

10. The stent graft introduction arrangement in combination with the fenestrated stent graft of claim 1, wherein the internal side arm extends toward the proximal end of the fenestrated stent graft.

11. The stent graft introduction arrangement in combination with the fenestrated stent graft of claim 1, wherein the internal side arm extends toward the distal end of the fenestrated stent graft.

12. A stent graft introduction arrangement in combination with a fenestrated stent graft,
the fenestrated stent graft comprising a main tubular body, distal end and a proximal end with a main lumen therethrough, a fenestration in the main body between the distal end and the proximal end of the fenestrated stent graft, and an internal side arm extending from the fenestration into the lumen of the main body and toward either the proximal or distal ends of the main body;
the introduction arrangement including an introducer, the introducer having a distal end intended to remain outside a patient in use and a proximal end, the proximal end of the introducer having a nose cone dilator and a retention arrangement to retain the fenestrated stent graft distally of the nose cone dilator, the fenestrated stent graft being retained on the introducer and a sheath on the introducer extending over the fenestrated stent graft to the nose cone dilator, an indwelling catheter extending from the distal end of the introducer through an introducer lumen in the introducer to the fenestrated stent graft, exiting from the introducer lumen at a distal end of the fenestrated stent graft and then entering the fenestration, then entering the internal side arm, then entering the main lumen and then extending toward the proximal end of the fenestrated stent graft, the indwelling catheter configured to receive a guide wire extending therethrough, whereby the guide wire can be extended beyond the nose cone dilator in use after the sheath is at least partially withdrawn from the fenestrated stent graft.

13. The stent graft introduction arrangement in combination with the fenestrated stent graft of claim 12, where the stent graft introduction arrangement to retain the fenestrated stent graft on the introducer includes trigger wires extending to the distal end of the introducer and release arrangements for separate release of the proximal and distal ends of the stent graft from the introducer.

14. The stent graft introduction arrangement in combination with the fenestrated stent graft of claim 12, where the fenestrated stent graft comprises a proximally extending exposed stent and the nose cone dilator comprises a distally facing capsule, the retention arrangement comprising the exposed stent being received into the distally facing capsule during deployment of the stent graft and release of the retention arrangement comprises advancing the nose cone dilator to release the exposed stent from the nose cone dilator.

15. The stent graft introduction arrangement in combination with the fenestrated stent graft of claim 12, where the fenestrated stent graft comprises a proximally extending exposed stent and a trigger wire system just distal of the nose cone dilator comprises the retention arrangement for the proximal end of the stent graft.

16. The stent graft introduction arrangement in combination with the fenestrated stent graft of claim 12, where the guide wire can be extended beyond the proximal end of the fenestrated stent graft in use after the sheath has been at least partially withdrawn from the fenestrated stent graft and before the retention arrangement to retain the fenestrated stent graft thereon distally of the nose cone dilator has been released.

17. The stent graft introduction arrangement in combination with the fenestrated stent graft of claim 12, wherein the internal side arm is configured to receive a leg extension.

18. The stent graft introduction arrangement in combination with the fenestrated stent graft of claim 12, wherein the internal side arm extends toward the proximal end of the fenestrated stent graft.

19. The stent graft introduction arrangement in combination with the fenestrated stent graft of claim 12, wherein the internal side arm extends toward the distal end of the fenestrated stent graft.

20. The stent graft introduction arrangement in combination with the fenestrated stent graft of claim 12, further comprising a second fenestration.

* * * * *